(12) United States Patent
Obeid et al.

(10) Patent No.: US 10,722,627 B1
(45) Date of Patent: Jul. 28, 2020

(54) BLOOD PUMP BEARING WITH INTEGRATED FLUID DIFFUSER/INDUCER SYSTEM

(71) Applicant: RBTS Inc., Phoenixville, PA (US)

(72) Inventors: Victor Obeid, Collegeville, PA (US); Michael D Neary, Bryn Mawr (ES); Edward Marlinski, Lansdale, PA (US)

(73) Assignee: RBTS Inc., Phoenixville, PA (US)

( * ) Notice: Subject to any disclaimer, the term of this patent is extended or adjusted under 35 U.S.C. 154(b) by 0 days.

(21) Appl. No.: 16/224,835

(22) Filed: Dec. 19, 2018

Related U.S. Application Data

(60) Provisional application No. 62/676,005, filed on May 24, 2018.

(51) Int. Cl.
| F16C 17/10 | (2006.01) |
| A61M 1/10 | (2006.01) |
| A61M 1/12 | (2006.01) |

(52) U.S. Cl.
CPC ........ *A61M 1/1029* (2014.02); *A61M 1/1013* (2014.02); *A61M 1/1086* (2013.01); *A61M 1/122* (2014.02); *A61M 2205/3334* (2013.01)

(58) Field of Classification Search
CPC .............. A61M 1/1013; A61M 1/1017; A61M 1/1029; F04D 29/0413; F04D 29/047; F04D 29/0513; F04D 29/057; F16C 17/047; F16C 17/105; F16C 17/33; F16C 17/1075; F16C 2360/44
See application file for complete search history.

(56) References Cited

U.S. PATENT DOCUMENTS

| 5,360,317 | A | 11/1994 | Clausen et al. |
| 5,588,812 | A | 12/1996 | Taylor et al. |
| 5,601,418 | A | 2/1997 | Ohara et al. |
| 5,683,231 | A | 11/1997 | Nakazawa et al. |
| 5,927,941 | A | 7/1999 | Kato et al. |
| 6,280,157 | B1 | 8/2001 | Cooper |
| 6,921,209 | B2 | 7/2005 | Hoffmann et al. |
| 7,416,525 | B2 | 8/2008 | Wampler et al. |
| 9,144,638 | B2 | 9/2015 | Zimmermann et al. |
| 9,629,947 | B2 * | 4/2017 | Yamane .................... F04D 3/00 |
| 2007/0004959 | A1 | 1/2007 | Carrier et al. |

(Continued)

FOREIGN PATENT DOCUMENTS

| WO | WO2010/029296 | 3/2010 |
| WO | WO2017/021465 | 2/2017 |

(Continued)

*Primary Examiner* — Phillip A Johnson
(74) *Attorney, Agent, or Firm* — Joseph E. Maenner; Maenner & Associates, LLC

(57) ABSTRACT

A shallow angle rotor bearing-vane system includes a smooth angled non-rotating journal component and a mating angled bearing/vane component, incorporating a plurality of integrated bearing/vanes oriented in a generally radial direction, which provide axial and radial load carrying support between the rotating components, and pumping action to the blood. The load carrying bearing surface situated in very close running proximity to the mating bearing component to prevent entry of red blood cells between the mating bearing surfaces, thereby creating a bearing operating in an elasto-hydrodynamic regime of mixed-lubrication or boundary-lubrication.

25 Claims, 14 Drawing Sheets

(56) References Cited

U.S. PATENT DOCUMENTS

| | | | |
|---|---|---|---|
| 2009/0022607 A1 | 1/2009 | Jordan et al. | |
| 2013/0170970 A1* | 7/2013 | Ozaki | A61M 1/101 415/203 |
| 2015/0314059 A1* | 11/2015 | Federspiel | A61M 1/1698 600/16 |
| 2016/0061209 A1* | 3/2016 | Steinseifer | F04D 29/22 417/423.12 |
| 2016/0121034 A1 | 5/2016 | Foster | |

FOREIGN PATENT DOCUMENTS

| | | |
|---|---|---|
| WO | WO2017/060254 | 4/2017 |
| WO | WO2018/078370 | 5/2018 |

* cited by examiner

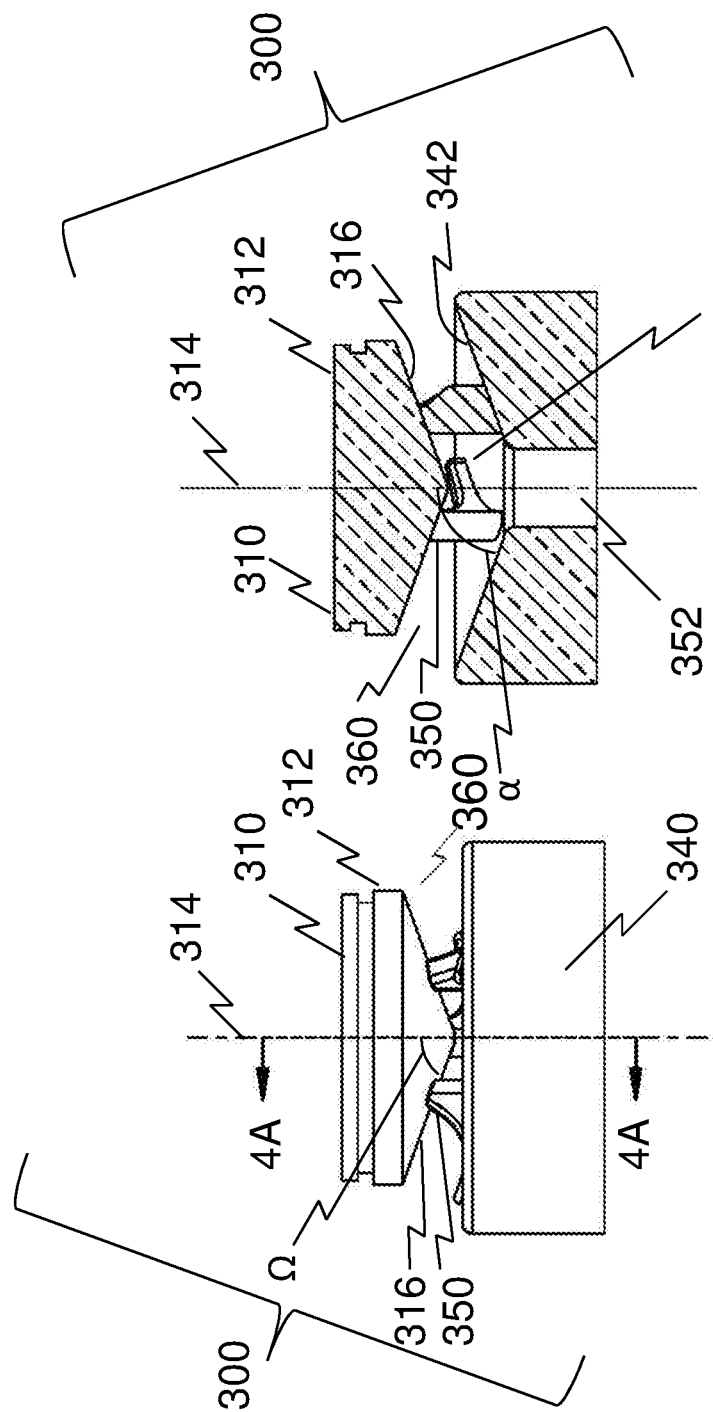

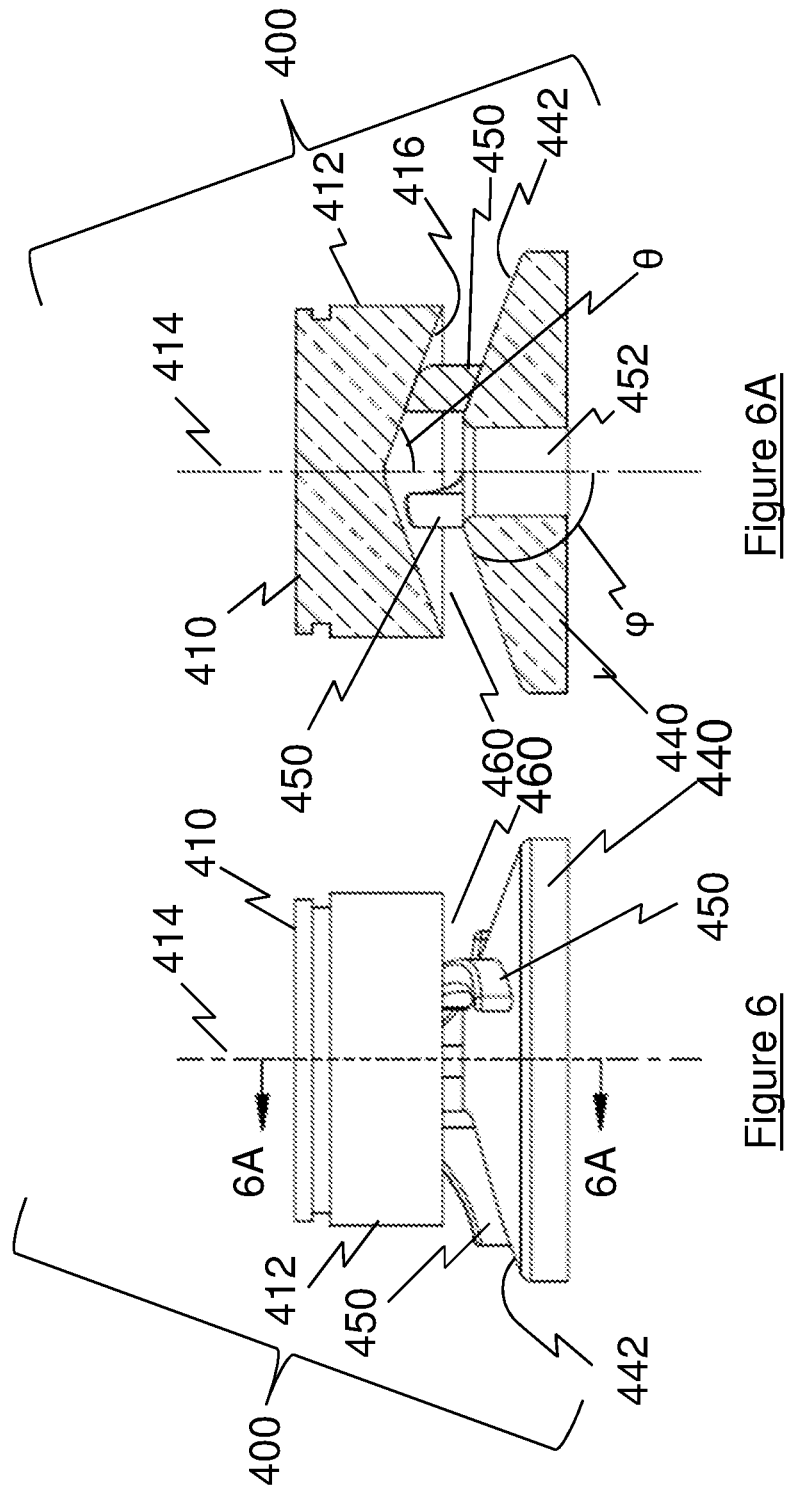

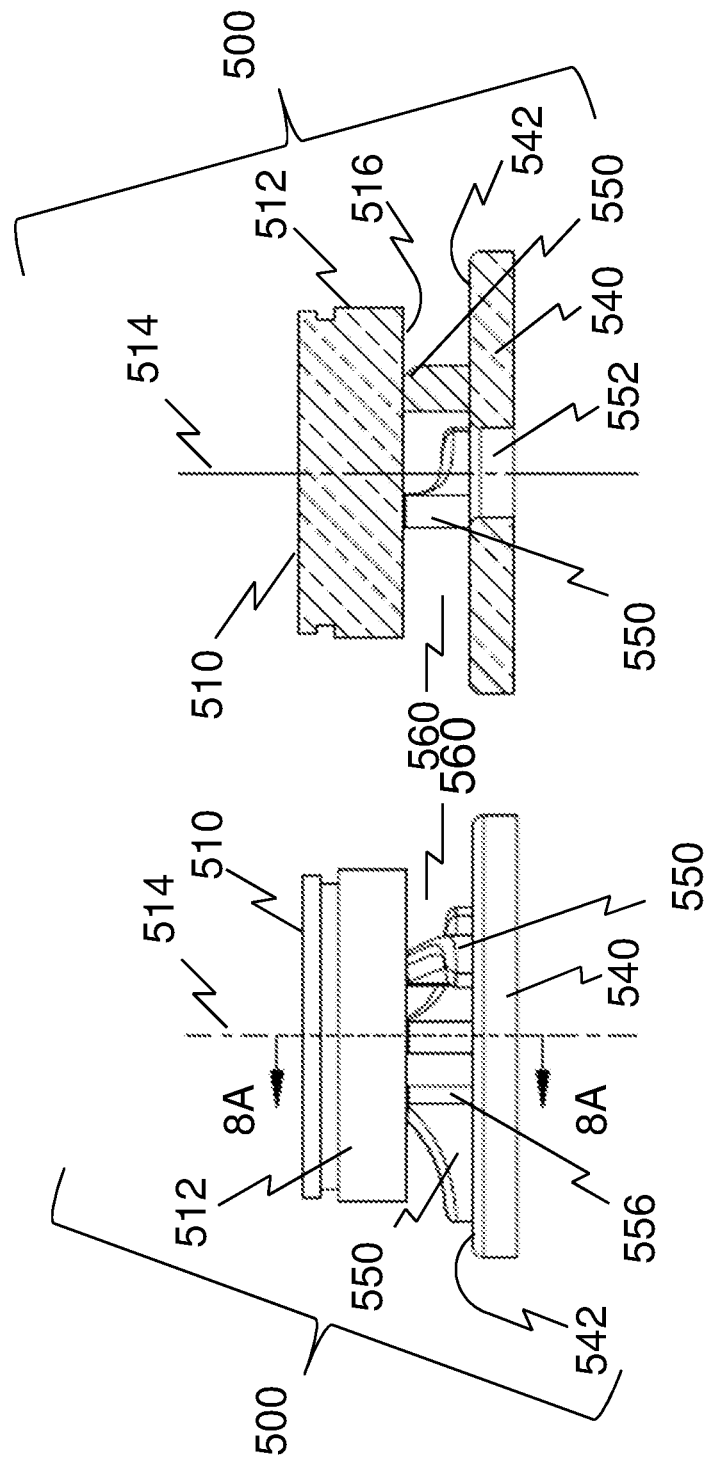

BLOOD PUMP BEARING WITH INTEGRATED FLUID DIFFUSER/INDUCER SYSTEM

CROSS-REFERENCE TO RELATED APPLICATION

The present application claims priority from U.S. Provisional Patent Application Ser. No. 62/676,005, filed on May 24, 2018, which is incorporated herein by reference in its entirety.

BACKGROUND OF THE INVENTION

Field of the Invention

The present invention relates to the field of rotary pumps. In particular, this invention is drawn to bearings for various pump rotor and stator configurations.

Description of the Related Art

Rotary blood pumps from a variety of manufacturers have been used to treat many types of heart function degradation over the past two decades. These pumps are commonly known as mechanical circulation support systems (MCSS) including, but not limited to, the class of devices known as ventricle assist devices or VADs. Such devices can be axial, radial, or mixed flow pumps designed either for intrathoracic, intracardiac, pericardiac, intra-aortic, or intra-arterial implantation. Over time, there has been a drive toward miniaturization of the pumps thereby requiring miniaturization of the bearing system components. One recurring problem with the current bearing designs is thrombus formation within the pumps, often starting in areas of blood stasis formed by the bearings and/or bearing support structure. A second recurring problem is blood hemolysis due to excessive shear stress being applied to the red blood cells as they pass through the rotor bearing system.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

By application of novel bearing geometry with integrated vanes rotating in an open annular area design, through which blood flow continually flushes, this invention eliminates stasis within the pump bearings solving the problem of thrombus formation. A purposefully designed ultra-thin elasto-hydrodynamic lubrication layer prevents red blood cells from entering the bearing running gap between bearing sliding surfaces (i.e. "bearing" and "journal"), thereby eliminating hemolysis within the bearing system. The use of select pairs of advanced engineering materials, designed with properly sized surfaces and curvatures, and tribological pressure-velocity (PV) analysis for such materials pairs, provides a zero wear to extremely-low wear bearing system. Lastly, the inventive use of integrated bearings and vanes to guide, support and locate the rotating assembly provides for a very compact bearing and vane structure which results in more compact blood pump designs where the vanes add active pumping to the blood flow within the bearing and pump assembly, to better flush, eliminate areas of flow stasis, remove heat, and augment the primary pumping objective.

This invention pertains to rotary pumps, rotary blood pumps, and rotary heart circulation assist pumps, in particular the bearings systems required to successfully support, locate, and guide the pump's rotating component with respect to the pump's non-rotating components. More specifically, this invention pertains to the addition of vane geometry to the bearing structure on the rotating component with an impeller shape or slinger shape, characterized hereinafter as an Integrated Bearing Diffuser (IBD) or Integrated Bearing Inducer (IBI) system, to develop pumping action within the bearing for primary objective of flushing the bearing annular open space. Depending on the pump design, secondary and tertiary benefits produced by the rotating IBD and IBI structures may be waste heat removal from the pump motor or pumping assist to the primary impeller.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 4 is a side elevational view of the bearing assembly of FIG. 3.

FIG. 4A is an axial cross section view of the bearing assembly of FIG. 4, taken along lines 4A-4A of FIG. 4.

FIG. 6 is a side elevational view of the bearing assembly of FIG. 5.

FIG. 6A is an axial cross section view of the bearing assembly of FIG. 6, taken along lines 6A-6A of FIG. 6.

FIG. 8 is a side elevational view of the bearing assembly of FIG. 7.

FIG. 8A is an axial cross section view of the bearing assembly of FIG. 8, taken along lines 8A-8A of FIG. 8.

DETAILED DESCRIPTION

Figure 1:
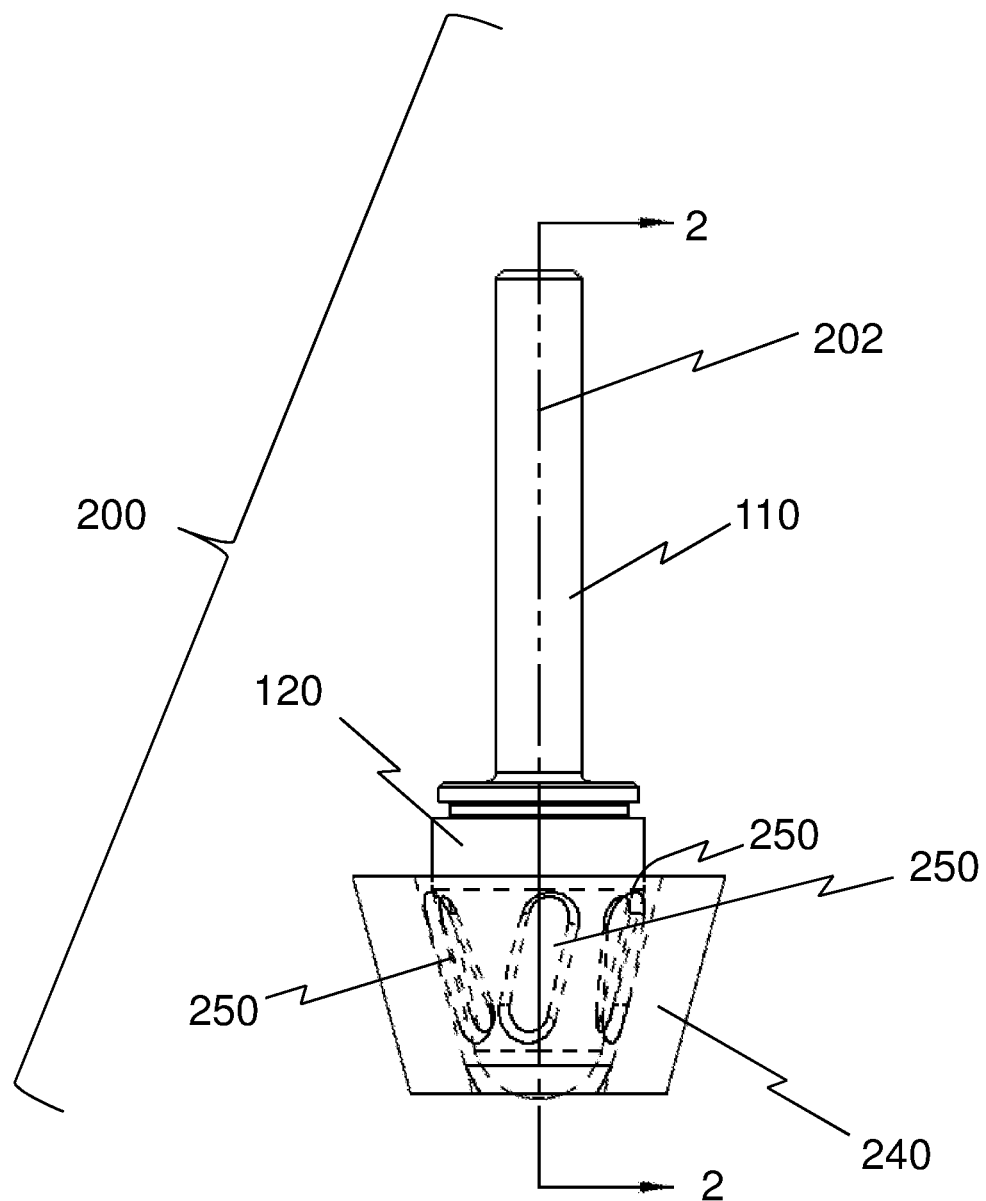
FIG. 1 is a side elevational view of a bearing assembly with oblong protruding bearing surfaces.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Bearing assemblies as described herein can be deployed in traditional motor configurations with a rotor located on the device central-axis affixed by a mounting pin, with a surrounding non-rotating stator. Alternatively, a pump employing the inventive bearing assembly can be of outrunner design wherein the central stator is stationary and the rotor is outboard of the stator, with the rotor rotating about the stator. Typical bearing assembly designs utilize stationary (non-rotating) protruding bearing structures across the flow path to guide and locate the rotating component in the blood flow path by means of a bearing surface. The existence of the fixed bearing protrusions or struts in the flow can be sources of flow stasis, which in turn can lead to thrombus formation near the bearings.

Figure 2:
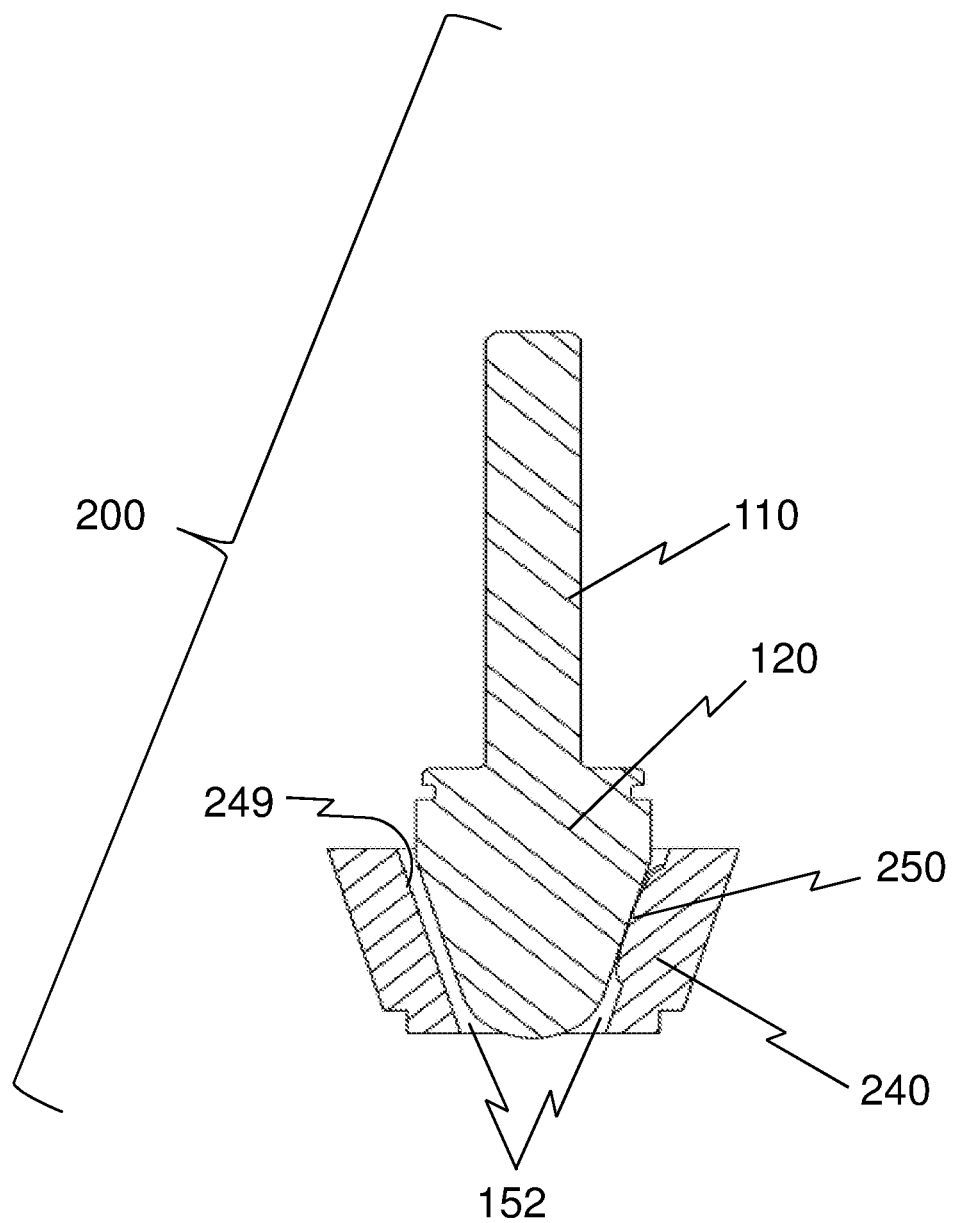
FIG. 2 is a cross section of the bearing assembly of FIG. 1 taken along lines 2-2 of FIG. 1.

Elongated vane shaped protrusions, either axially oriented or angularly oriented with respect to the central axis, can form bearing surfaces using a combination of materials such as metal, ceramic or engineered plastics. Illustrated in FIG. 1 and axial cross section FIG. 2 is a bearing assembly 200 having a tapered conical bearing 240 having an inner surface 249 and a plurality of bearing surfaces 250 extending radially inwardly of inner surface 249, with a single bearing surface 250 being shown in FIG. 2. In an exemplary embodiment, three radially spaced bearing surfaces 250 are provided, although those skilled in the art will recognize that more than three bearing surfaces 250 can be provided. Bearing assembly 200 further includes a smooth journal 120. The protruding bearing 250 generates a standoff gap 152 for flushing blood flow between the journal 120 and the bearing inner surface 249. Journal 120 includes an elongated shaft 110 extending away from bearing 240 such that a central axis 202 of assembly 200 extends along shaft 110.

The bearing implementations described in this invention often, but not always, have a generally conical or frustum shape of the bearing components being either concave or convex, as illustrated in FIGS. 4 and 6, that provides rotor support in both radial and axial directions to react hydraulic loads from the pumping action, centrifugal loads from rotating imbalance, and magnetic loads from rotor/stator offset. In this figure and others, the bearings and journals are illustrated as standalone components without the illustration of non-bearing pump components such as the rotor body, stator attachments, etc. For use in an actual blood pump the bearing components would be mechanically attached to the rotor and stator by fasteners, welding, adhesives, or other joining methods, or be integrally machined into a system component.

The load carrying surface area, or contact area, between the journal and the bearing is sized to generate an acceptable level of bearing lubrication film thickness, stiffness, damping, stability ratio, and a favorable pressure-velocity (PV) value between the two mating bearing components. The calculation of a pressure-velocity value for combinations of typical bearing materials is a technique common to the study of tribology in order to predict the success of a bearing system versus its expected loading and rotational speed operating-envelope. In general, empirical pin and disk testing of material pair combinations are conducted while varying the applied pressure and relative speeds in order to chart wear rates. Higher wear rates are associated with higher pressures or higher relative velocities between the two surfaces in sliding contact. Low PV values, for known combinations of preferred bearing materials, can result in zero wear to extremely low wear rates of the fixed and rotating bearing system components over the lifetime of the pump.

Sliding surface bearing surface geometries are often designed and fabricated such that geometry leading into the point of contact creates a thin converging wedge of fluid in the direction of flow between the components, regardless of the angle of approach of the blood velocity vector. Hydrodynamic bearing design requires a converging wedge shape in order for successful hydrodynamic film establishment and hydrodynamic bearing operation.

Certain embodiments of this invention often have, but are not limited to, a bearing geometry designed for a tight sliding-fit clearance operation between the journal and raised bearing/vane protrusions on the mating bearing component, thereby causing the bearing system to operate in an elasto-hydrodynamic regime of mixed-lubrication or boundary-lubrication. The tight clearance operation excludes the entry of red blood cells between the bearing running surfaces, and thus does not damage or rupture the erythrocytes and thereby prevents hemolysis within the bearing.

Figure 3:
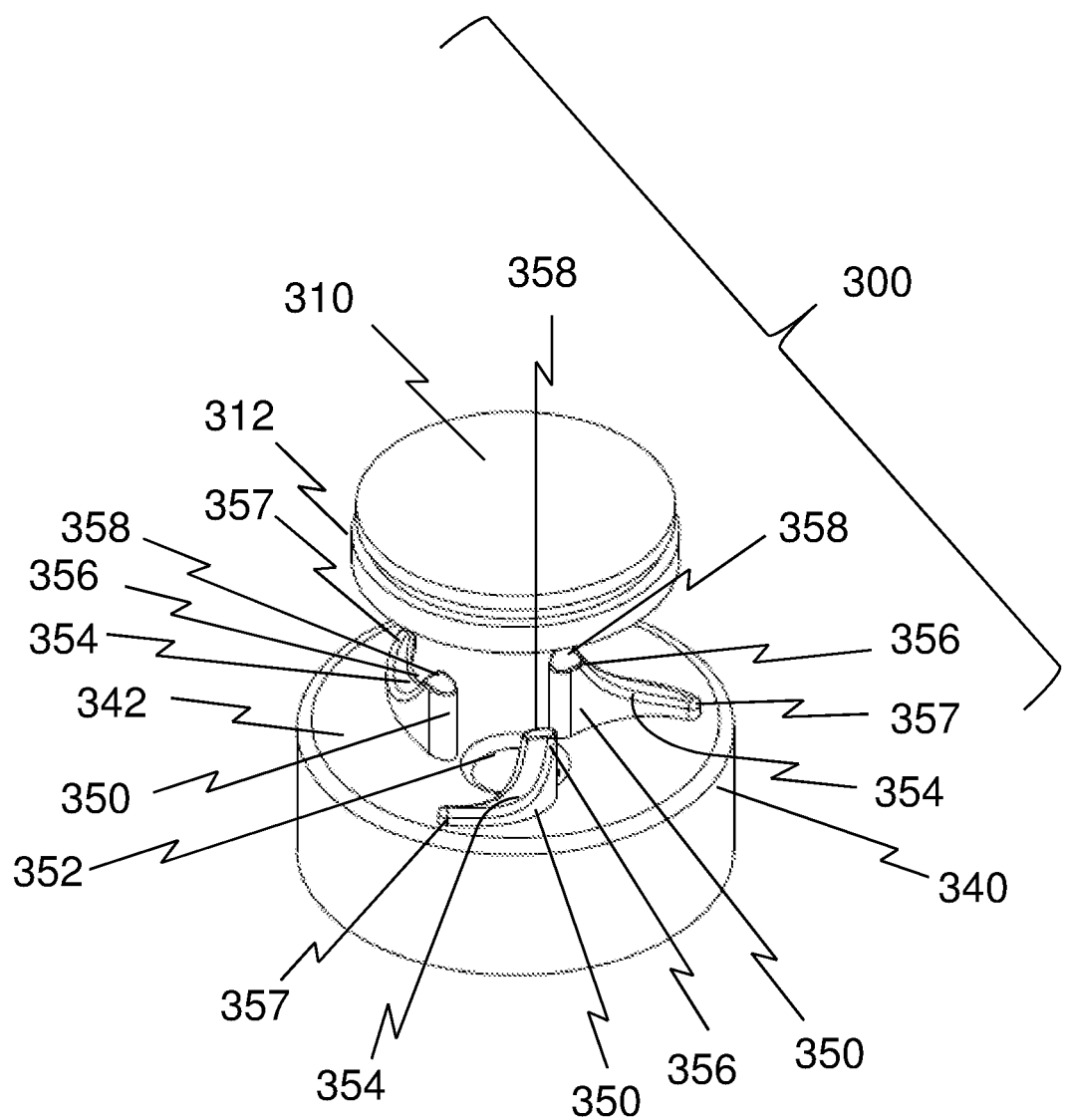
FIG. 3 is a perspective view of a three point-of-contact concave bearing assembly with integrated vanes according to a first exemplary embodiment of the invention.

An alternative exemplary embodiment of a bearing assembly 300 according to the present invention is shown in FIGS. 3-4A Bearing assembly 300 includes a journal 310 having a body 312 extending along a central longitudinal axis 314, which coincides with an axis of rotation of bearing assembly 300. Those skilled in the art, however, will recognize that two bearing assemblies 300 can support a stator 310 and a rotor 340 within a pump. Body 312 includes a convex conical face 316 for engagement with a bearing 340. In an exemplary embodiment, face 316 has a cone angle $\Omega$ of about 70 degrees with respect to longitudinal axis 314, although those skilled in the art will recognize that other angles can be provided.

Bearing 340 includes a concave face 342 with three integral bearing/vane structures 350 radially spaced about a longitudinal opening 352 that is centered along longitudinal axis 314. In an exemplary embodiment, face 342 has a cone angle $\alpha$ of about 70 degrees with respect to longitudinal axis 314, although those skilled in the art will recognize that other angles can be provided.

FIG. 3 shows a rotor 340 having three arcuate bodies 354, each with a higher profiled end 356 located radially inwardly of structure 350 that tapers to a lower profiled end 357 located radially outwardly of structure 350. Those skilled in the art, however, will recognize that rotor 340 can have more than three arcuate bodies 354.

The physical contact between the convex face 316 and the three bearing/vane structures 350 can range from full-surface contacts to very small areas, otherwise known as lands 358, of contact, located at the higher profiled ends or section 356 of each bearing/vane structure 350. Such lands 358 can be formed by mechanical deformation, machining, or abrasive methods in order to create a conformal, tight sliding-fit clearance between the parts. Three bearing/vane structures 350 are used to center journal 310 along longitudinal axis 314.

Bearing/vane structures 350 are sized to provide a gap 360 between face 316 and face 342 to allow for the flushing passage of fluid through gap 360 as the fluid is being pumped. In an exemplary embodiment, the gap 360 between face 316 and land 358 is designed to support an elasto-hydrodynamic lubrication film which is small enough to prevent red blood cells from flowing through the gap 360 between face 316 and land 358.

Figure 4B:
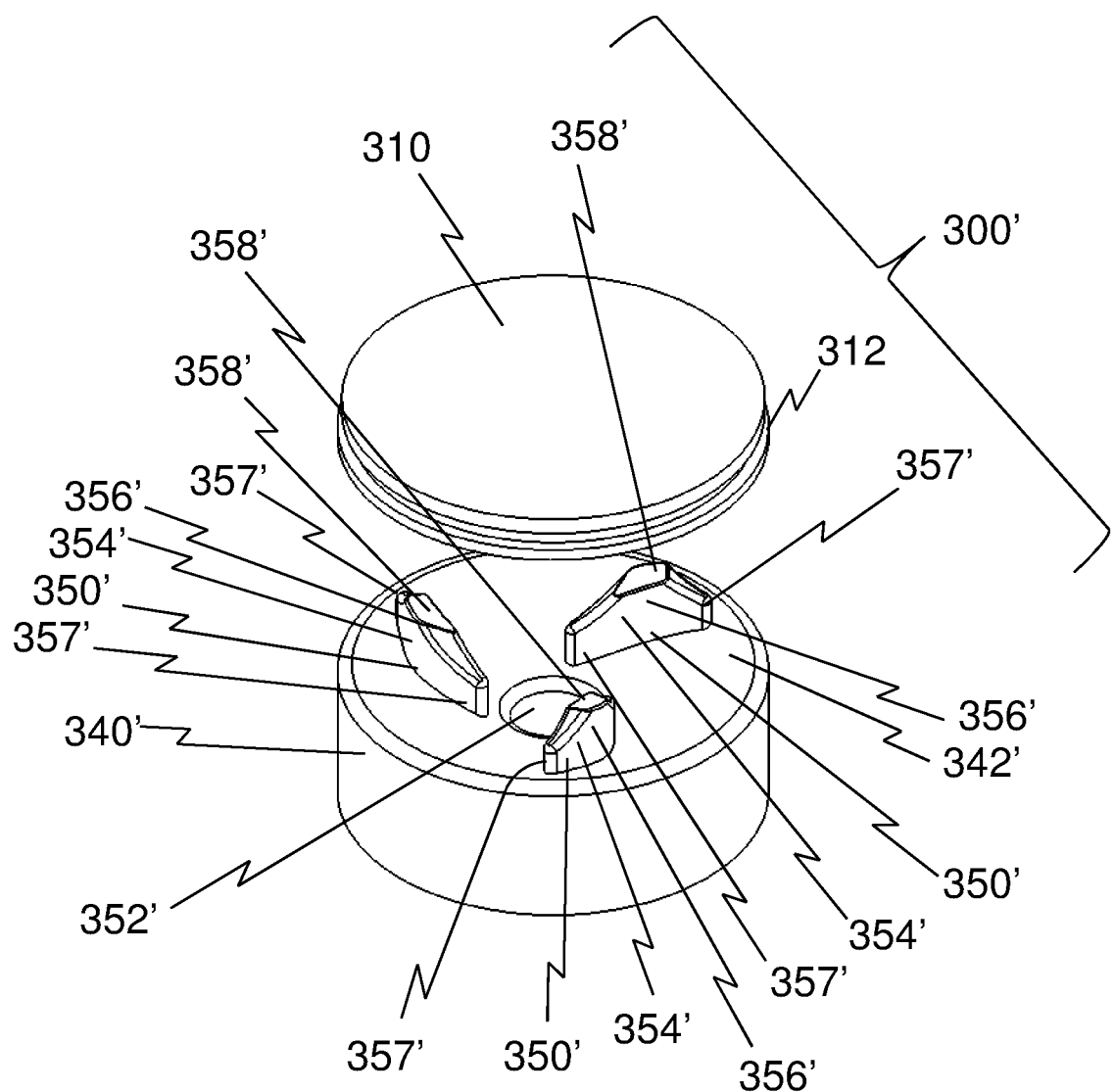
FIG. 4B is a perspective view of a three point-of-contact concave bearing assembly with integrated vanes according to an alternative exemplary embodiment of the invention.

FIG. 4B shows an alternative embodiment of a bearing assembly 300' according to the present invention. Bearing assembly 300' is similar to bearing assembly 300, but includes a bearing 340' having three arcuate bodies 354' mounted on a bearing face 342', each body 354' having a higher profiled section 356' located radially centered of structure 350' that tapers to lower profiled ends 357' located radially inwardly and outwardly of lands 358'.

Figure 4C:
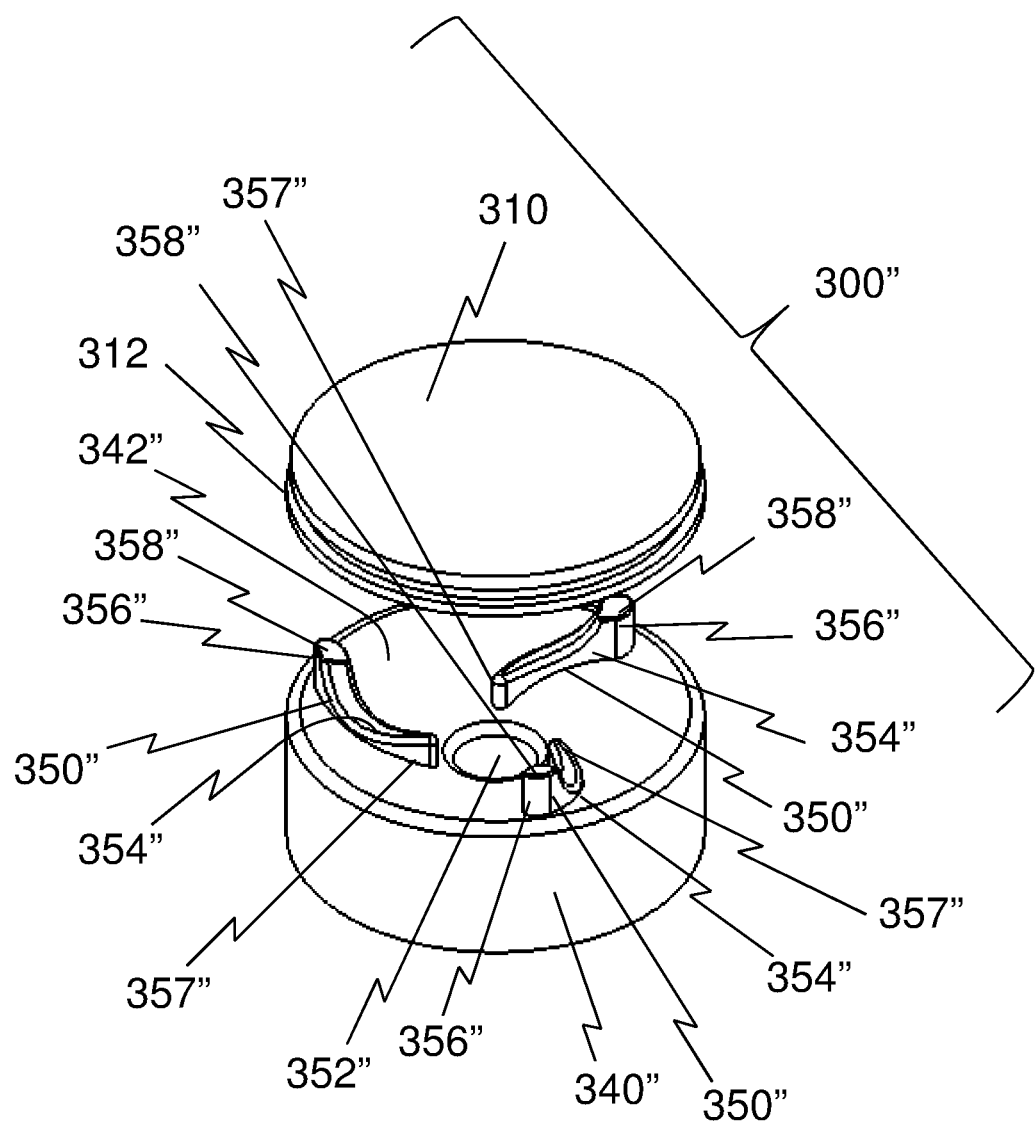
FIG. 4C is a perspective view of a three point-of-contact concave bearing assembly with integrated vanes according to another alternative exemplary embodiment of the invention.

FIG. 4C shows an alternative embodiment of a bearing assembly 300" according to the present invention. Bearing assembly 300" is similar to bearing assembly 300, but includes a bearing 340" having three arcuate bodies 354" mounted on a bearing face 342", each body 354" having a higher profiled end 356" located radially outwardly of structure 350" that tapers to a lower profiled end 357" located radially inwardly of structure 350".

FIGS. 3, 4B, and 4C show three bearing/vane structures 350, 350', 350" each having a respective plurality of arcuate bodies 354, 354', 354" with displayed configurations, although those skilled in the art will recognize that other configurations can be provided.

Figure 5:
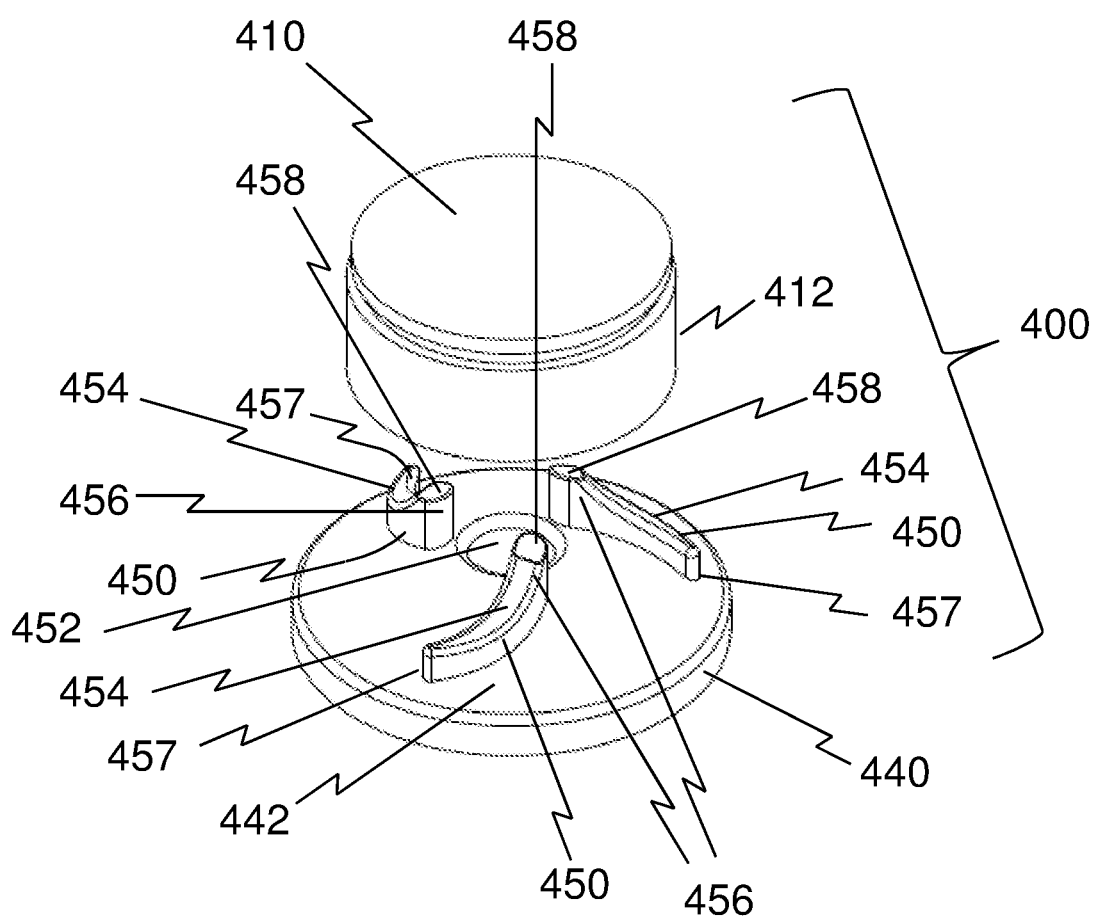
FIG. 5 is a perspective view of a three point-of-contact convex bearing assembly with integrated vanes according to a second exemplary embodiment of the present invention.

FIGS. 5-6A show a second exemplary embodiment of a bearing assembly 400. Similar to bearing assembly 300, bearing assembly 400 includes a journal 410 having a body 412 extending along a central longitudinal axis 414, which coincides with an axis of rotation of bearing assembly 400. Body 412 includes a concave conical face 416 for engagement with a bearing 440. In an exemplary embodiment, face 416 has a cone angle $\theta$ of about 70 degrees with respect to longitudinal axis 414, although those skilled in the art will recognize that other angles can be provided.

Bearing 440 includes a convex face 442 with three integral bearing/vane structures 450 radially spaced about a longitudinal opening 452 that is centered along longitudinal axis 414. In an exemplary embodiment, face 442 has a cone angle $\varphi$ of about 70 degrees with respect to longitudinal axis 414, although those skilled in the art will recognize that other angles can be provided.

Bearing/vane structures 450 each have an arcuate body 454, with a higher profiled end 456 located radially inwardly of structure 450 that tapers to a lower profiled end 457 located radially outwardly of structure 450.

The physical contact between the journal face 416 and the three bearing/vane structures 450 can range from full-surface contacts to very small areas, otherwise known as lands 458, of contact, located at the higher profiled ends or section 456 of each bearing/vane structure 450. Such lands 458 can be formed by mechanical deformation, machining, or abrasive methods in order to create a conformal, tight sliding-fit clearance between the parts. Three bearing/vane structures 450 are used to center journal 410 along longitudinal axis 414 and axially locate the journal 410 with respect to the bearing 440.

Bearing/vane structures 450 are sized to provide a gap 460 between face 416 and face 442 to allow for the flushing passage of fluid through gap 460 as the fluid is being pumped. In an exemplary embodiment, the gap 460 between face 416 and land 458 is designed to support an elasto-hydrodynamic lubrication film, which is small enough to prevent red blood cells from flowing through the gap 460 between face 416 and land 458.

Figure 6B:
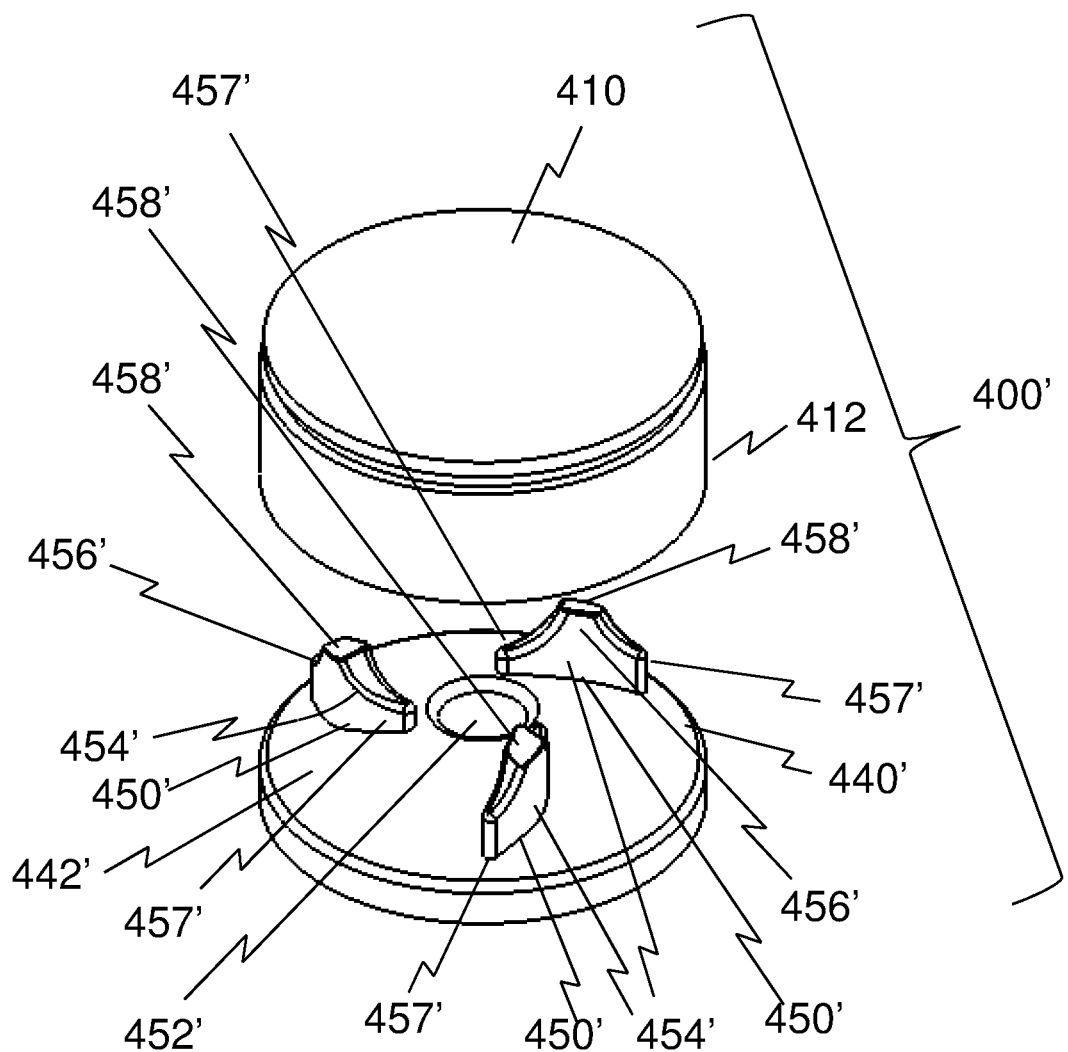
FIG. 6B is a perspective view of a three point-of-contact convex bearing assembly with integrated vanes according to an alternative exemplary embodiment of the invention.

FIG. 6B shows an alternative embodiment of a bearing assembly 400' according to the present invention. Bearing assembly 400' is similar to bearing assembly 400, but includes a bearing 440' having three arcuate bodies 454' mounted on a bearing face 442', each body 454' having a higher profiled section 456' located radially centered of structure 450' that tapers to lower profiled ends 457' located radially inwardly and outwardly of lands 458'.

Figure 6C:
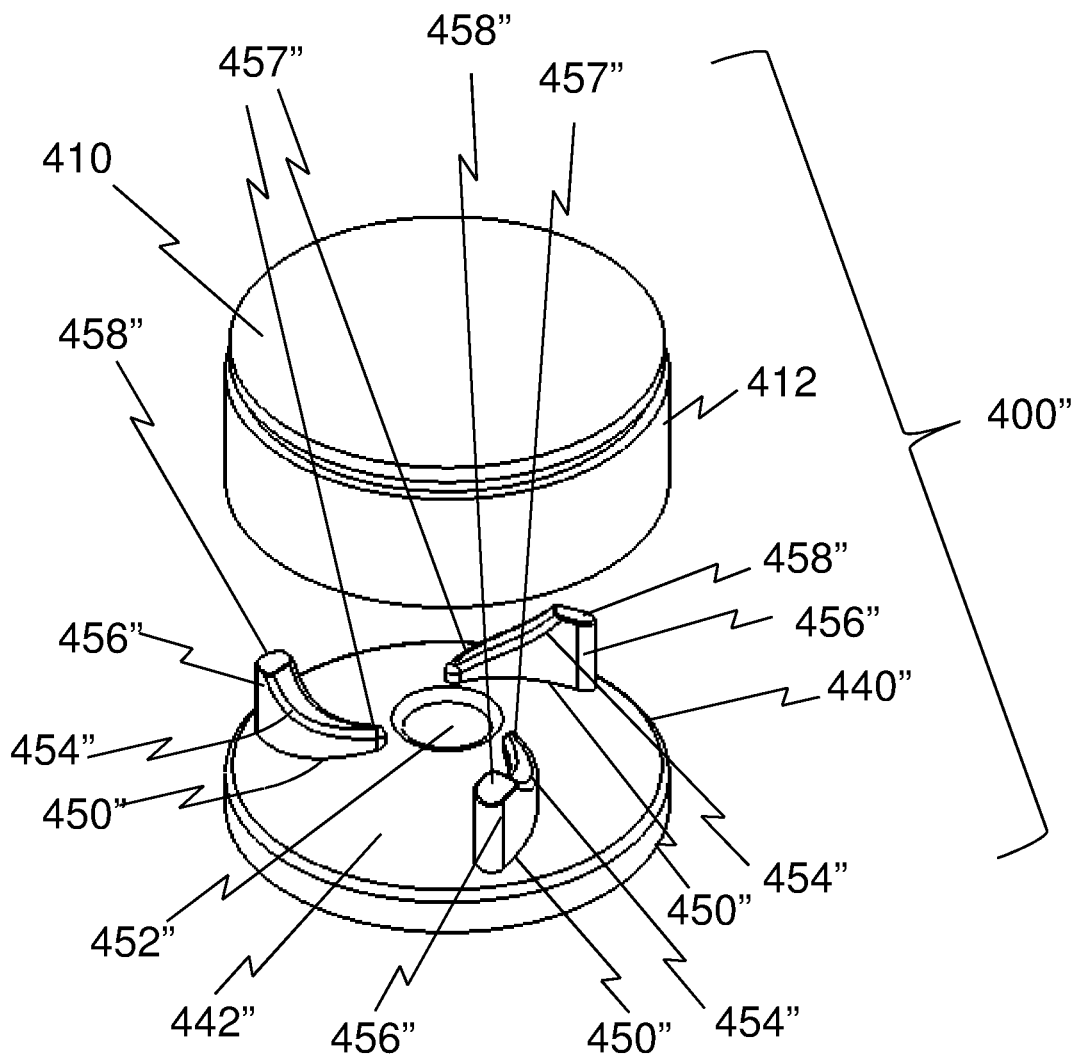
FIG. 6C is a perspective view of a three point-of-contact convex bearing assembly with integrated vanes according to another alternative exemplary embodiment of the invention.

FIG. 6C shows an alternative embodiment of a bearing assembly 400" according to the present invention. Bearing assembly 400" is similar to bearing assembly 400, but includes a bearing 440" having three arcuate bodies 454" mounted on a bearing face 442", each body 454" having a higher profiled end 456" located radially outwardly of structure 450" that tapers to a lower profiled end 457" located radially inwardly of structure 450".

FIGS. 5, 6B, and 6C show three bearing/vane structures 450, 450', 450" each having a respective plurality of arcuate bodies 454, 454', 454" with displayed configurations, although those skilled in the art will recognize that other configurations can be provided.

Figure 7:
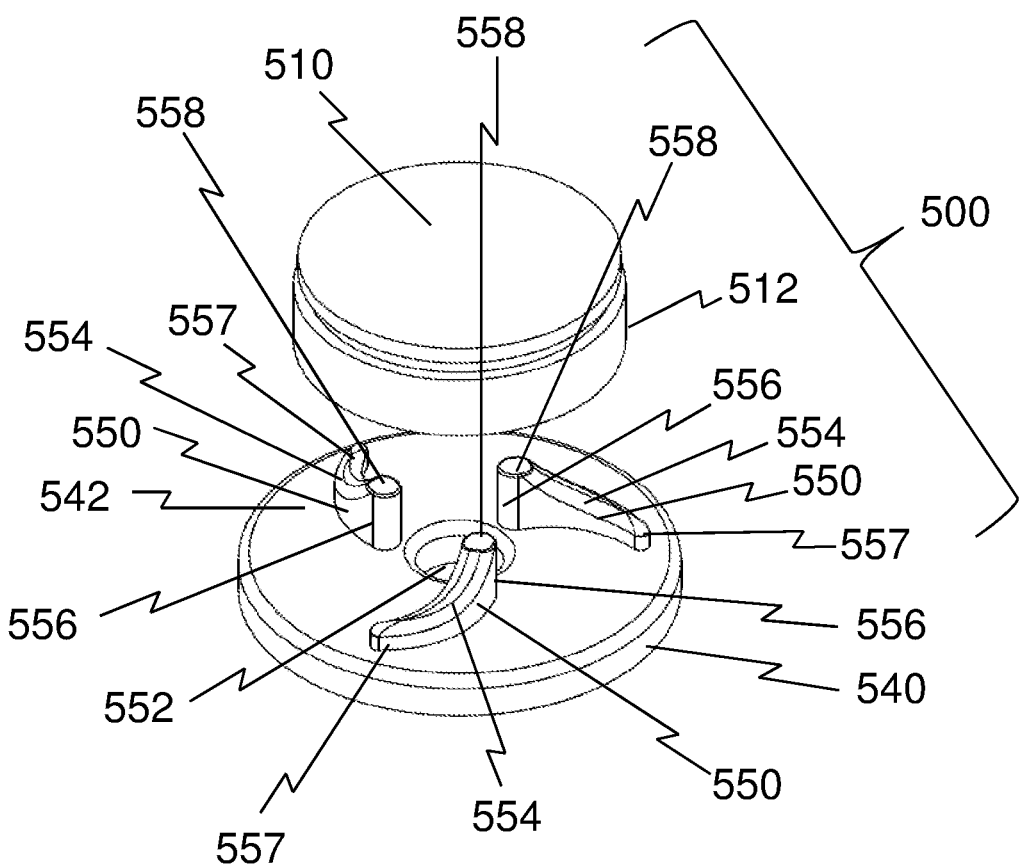
FIG. 7 is a perspective view of a three point-of-contact flat bearing assembly with integrated vanes according to a third exemplary embodiment of the present invention.

FIGS. 7-8A show a third exemplary embodiment of a bearing assembly 500. Similar to bearing assemblies 300 and 400, bearing assembly 500 includes a journal 510 having a body 512 extending along a central longitudinal axis 514, which coincides with an axis of rotation of bearing assembly 500. Unlike journals 310, 410, body 512 includes a flat face 516 for engagement with a bearing 540.

Bearing 540 includes a flat face 542 with three integral bearing/vane structures 550 radially spaced about a longitudinal opening 552 that is centered along longitudinal axis 514. Bearing/vane structures 550 each have an arcuate body 554, with a higher profiled end 556 located radially inwardly of structure 550 that tapers to a lower profiled end 557 located radially outwardly of structure 550.

The physical contact between the journal face 516 and the three bearing/vane structures 550 can range from full-surface contacts to very small areas, otherwise known as lands 558, of contact, located at the higher profiled ends or section 556 of each bearing/vane structure 550. Such lands 558 can be formed by mechanical deformation, machining, or abrasive methods in order to create a conformal, tight sliding-fit clearance between the parts. Three bearing/vane structures 550 are used to axially support the journal 510 away from the bearing 540.

Bearing/vane structures 550 are sized to provide a gap 560 between face 516 and face 542 to allow for the flushing passage of fluid through gap 560 as the fluid is being pumped. In an exemplary embodiment, the gap 560 between face 516 and land 558 is designed to support an elastohydrodynamic lubrication film, which is small enough to prevent red blood cells from flowing through the gap 560 between face 516 and land 558.

Figure 8B:
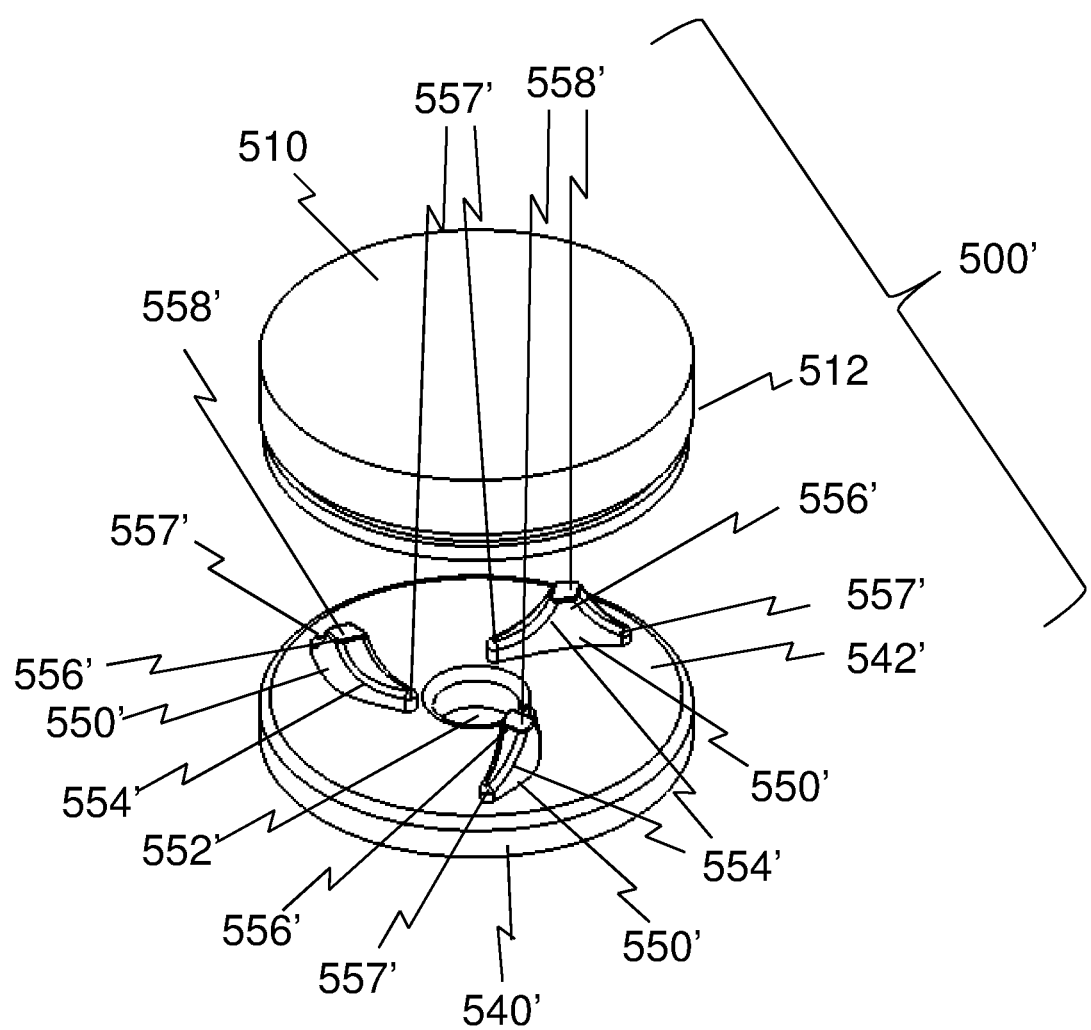
FIG. 8B is a perspective view of a three point-of-contact flat bearing assembly with integrated vanes according to an alternative exemplary embodiment of the invention.

FIG. 8B shows an alternative embodiment of a bearing assembly 500' according to the present invention. Bearing assembly 500' is similar to bearing assembly 500, but includes a bearing 540' having three arcuate bodies 554' mounted on a bearing face 542', each body 554' having a higher profiled section 556' located radially centered of structure 550' that tapers to lower profiled ends 557' located radially inwardly and outwardly of lands 558'.

Figure 8C:
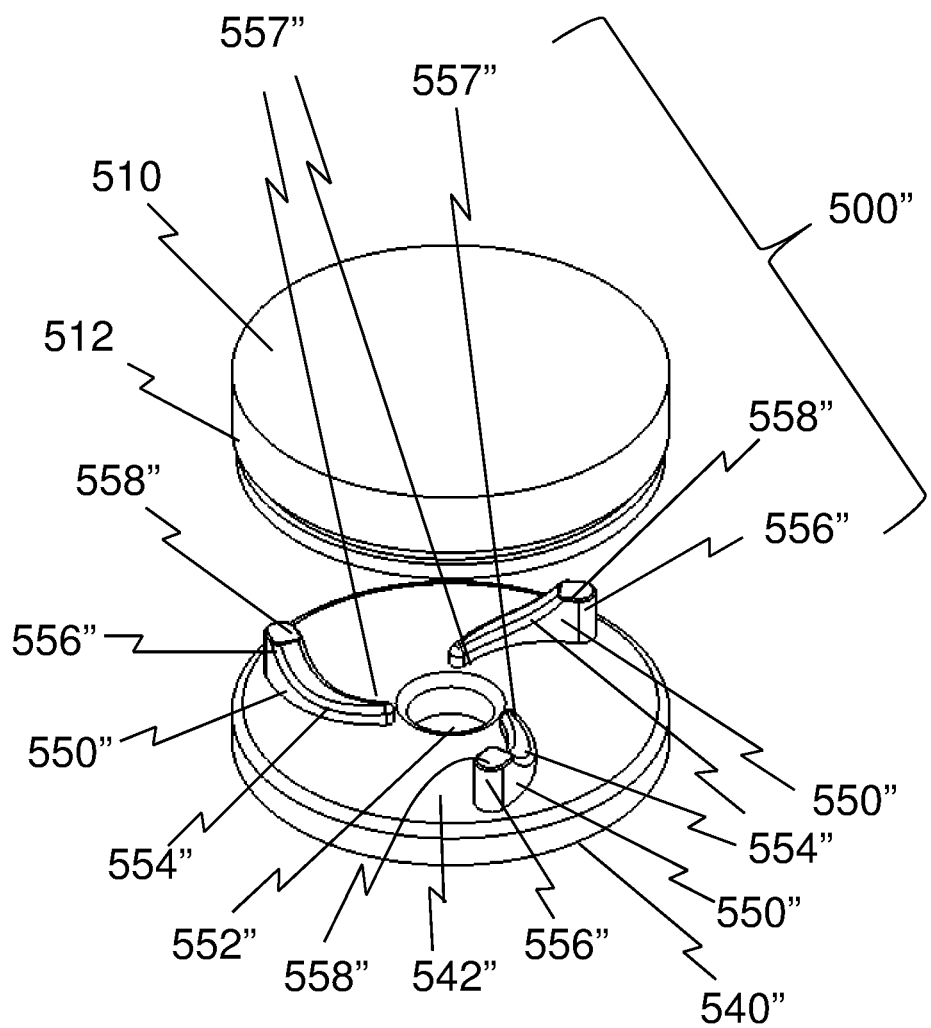
FIG. 8C is a perspective view of a three point-of-contact flat bearing assembly with integrated vanes according to another alternative exemplary embodiment of the invention.

FIG. 8C shows an alternative embodiment of a bearing assembly 500" according to the present invention. Bearing assembly 500" is similar to bearing assembly 500, but includes a bearing 540" having three arcuate bodies 554" mounted on a bearing face 542", each body 554" having a higher profiled end 556" located radially outwardly of structure 550" that tapers to a lower profiled end 557" located radially inwardly of structure 550".

FIGS. 7, 8B, and 8C show three bearing/vane structures 550, 550', 550" each having a respective plurality of arcuate bodies 554, 554', 554" with displayed configurations, although those skilled in the art will recognize that other configurations can be provided.

Operation and other features of bearing assembly 300 will now be discussed. Those skilled in the art will recognize that the operation and other features of bearing assemblies 400 and 500 are similar, if not identical. In practice, either journal 310 or bearing 340 can be rotatable with respect to the other of journal 310 and bearing 340. In certain embodiments of this invention, when incorporated into a pump and dependent upon the pump rotor and motor stator design, preferably the bearing 340 rotates to transfer mechanical pumping energy to the fluid being pumped.

Bearing assembly 300 can be fabricated from materials that exhibit superior qualities with respect to bearing performance, including low sliding friction, resistance to wear, mechanical stability, and thermal stability. This includes the classes of materials such as, but not limited to, metals such as titanium or stainless steel, ceramics such as sapphire, aluminum oxide, yttria-stabilized zirconia ceramic, silicon carbide, and also engineered plastics such as poly ether ether ketone ("PEEK"), ultra high molecular weight polyethylene ("UHMWPE"), polyetherimide such as ULTEM®, polytetrafluoroethylene ("PTFE"), or surface treated and coated (STAC) metals with coatings such as diamond-like carbon (DLC), and others, optimized for sliding surface applications. In some embodiments, only the contact engaging elements, such as protrusions 250 and lands 358, 458, 558 can be constructed from such materials.

In operation, the rotation of the bearing 340 and vane structures 350 about longitudinal axis 314 generates a diffusive motion of the fluid in the outward discharge direction while a contra-rotation of the vane structures 350 induces the fluid motion in an inward direction. In either case, the working fluid can be provided ingress or egress though the preferably, but not necessarily, centrally located opening 352 located along the central longitudinal axis 314.

The contact areas 358 of the vane structures 350 are optimally sized with respect to pressure-velocity (PV) value, sized specifically to accommodate the device's loading generated mechanically, hydraulically, and electromagnetically. The vane structures 350 can be full height and also provide bearing support area along the complete vane length, but are preferably lower profile to transfer sufficient mechanical energy to the working fluid in order to diffuse outward, or to induce inward, at such a flow rate to insure continuous and full flow-field flushing, thereby preventing areas of stasis. Reduced height vane structures 350 can impart sufficient energy to the fluid flow to achieve the flushing objective, while presenting a lower drag force and reduced surface area to the flow field. The geometry of the vane structures 350 can be straight, or arcuate (as shown) with such a curve to optimize rotational mechanical energy transfer into hydraulic energy, typified as fluid pressure increase or fluid velocity increase.

Dependent upon the pump design requirements, the bearing face 342 can be either convex or concave with respect to a plane drawn perpendicular to the axis 314, or the bearing face 342 can be of a configuration such that all three bearing surfaces 358 are flat and coplanar and perpendicular to the axis 314. The angle and gap width of the fluid flow gap 360 between the rotating bearing 340 and the journal 310 is sized via methods such as computational fluid dynamics (CFD) to numerically model the fluid flow for flow streamlines, localized pressure fields, and velocity vector mapping. Consideration of CFD results aides in optimal design of particular angles and component shapes resulting in, maximum continuous flushing to eliminate thrombus causing areas of recirculation or stasis, and minimal shear stress applied to the red blood cells, minimizing risk of hemolysis.

This fluid flushing is secondarily advantageous to remove heat from the bearings to improve bearing performance, and may further to cool the pump thereby helping to keep the system at an acceptable operational temperature. Further, the continuous heat removal may help maintain the motor stator at a safe temperature level for contact with body tissue such as heart myocardium or blood.

It will be further understood that various changes in the details, materials, and arrangements of the parts which have been described and illustrated in order to explain the nature of this invention may be made by those skilled in the art without departing from the scope of the invention as expressed in the following claims.

We claim:

1. A rotor bearing assembly comprising:
   a journal having a central longitudinal axis extending therethrough; and
   a mating bearing having a plurality of structures extending outwardly therefrom and in engagement with the journal, wherein the journal is spaced from the bearing by a gap for fluid flushing and for forming an elasto-hydrodynamic boundary lubrication film.

2. The rotor bearing assembly according to claim 1, wherein the journal comprises a conical journal face extending at an angle relative to the central longitudinal axis and wherein the bearing comprises a conical bearing face extending at the angle relative to the central longitudinal axis.

3. The rotor bearing assembly according to claim 2, wherein the conical journal comprises a convex journal face.

4. The rotor bearing assembly according to claim 2, wherein the conical journal comprises a concave journal face.

5. The rotor bearing assembly according to claim 2, wherein the bearing comprises a flat bearing face.

6. The rotor bearing assembly according to claim 1, wherein the plurality of structures comprises a plurality of protrusions.

7. The rotor bearing assembly according to claim 6, wherein the plurality of protrusions each comprises an arcuate protrusion.

8. The rotor bearing assembly according to claim 7, wherein the plurality of protrusions each comprises an oblong protrusion.

9. The rotor bearing assembly according to claim 8, wherein each of the plurality of oblong protrusions extends obliquely with respect to the central longitudinal axis.

10. The rotor bearing assembly according to claim 1, wherein the plurality of structures comprises a plurality of vanes.

11. The rotor bearing assembly according to claim 10, wherein each of the plurality of vanes comprises a vane body tapering from a lower radially outward portion to a higher radially inward portion.

12. The rotor bearing assembly according to claim 11, wherein the vane body comprises a land at the higher radially inward portion.

13. The rotor bearing assembly according to claim 10, wherein each of the plurality of vanes comprises a vane body tapering from a higher radially outward portion to a lower radially inward portion.

14. The rotor bearing assembly according to claim 13, wherein the vane body comprises a land at the higher radially outward portion.

15. The rotor bearing assembly according to claim 10, wherein each of the plurality of vanes comprises a vane body tapering from a higher radially centered portion to a lower radially inward and outward portion.

16. The rotor bearing assembly according to claim 15, wherein the vane body comprises a land at the higher radially outward portion.

17. The rotor bearing assembly according to claim 10, wherein each of the vane bodies is arcuately shaped.

18. The rotor bearing assembly according to claim 17, wherein the structures comprise vanes having a tapered body such that only a land portion of the body engages the journal.

19. The rotor bearing assembly according to claim 17, wherein the structures are in contact with the journal along substantially the length of the protrusions.

20. The rotor bearing assembly according to claim 17, wherein one of the journal and the bearing is non-rotating and the other of the journal and the bearing is rotatable.

21. The rotor bearing assembly according to claim 1, wherein the structures center the journal and the bearing along the central longitudinal axis.

22. The rotor bearing assembly according to claim 1, wherein the gap between the journal and bearing land forms an elasto-hydrodynamic regime of mixed- or boundary-lubrication.

23. The rotor bearing assembly according to claim 1, wherein the bearing comprises protruding structures and wherein the gap between the journal and bearing is for flushing of the bearing protruding structures.

24. The rotor bearing assembly according to claim 1, wherein the structures are constructed from a material selected from the group consisting of sapphire, Silicon carbide, yttria-stabilized zirconia ceramic, engineered plastics, PEEK, UHMWPE, ULTEM, PTFE, diamond-like carbon, and titanium.

25. A rotor bearing assembly comprising:
   a journal; and
   a mating bearing having a plurality of integrated structures extending in a generally radial direction and engaging the journal, wherein the structures provide axial and radial load carrying support between the journal and the bearing, and pumping action to a fluid flowing through the assembly.

* * * * *